United States Patent [19]

Dolfini et al.

[11] 4,062,842

[45] Dec. 13, 1977

[54] METHOD FOR PREPARING 7-SUBSTITUTED CEPHALOSPORINS AND 6-SUBSTITUTED PENICILLINS BY REPLACEMENT OF SULFUR-CONTAINING GROUPS

[75] Inventors: Joseph E. Dolfini, Cincinnati, Ohio; William A. Slusarchyk, Belle Mead; William H. Koster, Pennington, both of N.J.

[73] Assignee: E. R. Squibb & Sons, Inc., Princeton, N.J.

[21] Appl. No.: 650,221

[22] Filed: Jan. 19, 1976

Related U.S. Application Data

[63] Continuation-in-part of Ser. No. 394,943, Sept. 6, 1973, abandoned, and a continuation-in-part of Ser. No. 394,713, Sept. 6, 1973, abandoned, said Ser. No. 394,943 is a continuation-in-part of Ser. No. 312,436, Dec. 6, 1972, abandoned, said Ser. No. 394,713 is a continuation-in-part of Ser. No. 312,472, Dec. 6, 1972, abandoned.

[51] Int. Cl.$^2$ .................. C07D 501/04; C07D 499/04
[52] U.S. Cl. .................. 260/239.1; 544/21; 424/246; 424/271
[58] Field of Search .................. 260/243 C, 239.1

[56] References Cited

U.S. PATENT DOCUMENTS 3,778,432  12/1973  Pines .................. 260/243 C

*Primary Examiner*—Nicholas S. Rizzo
*Attorney, Agent, or Firm*—Lawrence S. Levinson; Merle J. Smith; Stephen B. Davis

[57] ABSTRACT

Disclosed is a method for replacing 7-lower alkylthio and 7-arylthio groups from cephalosporins with lower alkanoyloxy, lower alkoxy, aryloxy, aroyloxy, amino, lower alkylamino and azido moieties, and for replacing 6-lower alkylthio and 6-arylthio groups from penicillins with lower alkanoyloxy, lower alkoxy, aryloxy, aroyloxy, amino, lower alkyl amino, and azido moieties.

23 Claims, No Drawings

METHOD FOR PREPARING 7-SUBSTITUTED CEPHALOSPORINS AND 6-SUBSTITUTED PENICILLINS BY REPLACEMENT OF SULFUR-CONTAINING GROUPS

This application is a continuation-in-part of copending applications Ser. No. 394,943 filed on Sept. 6, 1973, now abandoned and Ser. No. 394,713 filed on Sept. 6, 1973, now abandoned. Ser. No. 394,943 was a continuation-in-part of Ser. No. 312,436 filed on Dec. 6, 1972, now abandoned, and Ser. No. 394,713 was a continuation-in-part of Ser. No. 312,472 filed on Dec. 6, 1972, now abandoned.

Cephalosporins and penicillins are of considerable interest to the pharmaceutical industry. Presently compounds of this type are being employed as potent antimicrobials. As in the case of tetracyclines, researchers are now trying to improve on the activity of these antibiotics by modifying the naturally occurring cephalosporins and penicillins. Unfortunately, most antibiotics are quite complex and therefore simple reactions cannot be utilized to introduce the desired modifications. Usually considerable effort must be extended to devise a method for modifying such complex entities. Herein is described such a procedure which gives rise to useful antibacterial cephalosporins and penicillins.

This invention relates to a method for the conversion of cephalosporins of the formula:

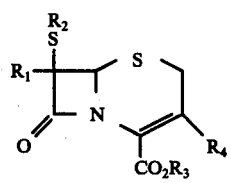

I into compounds of the formula:

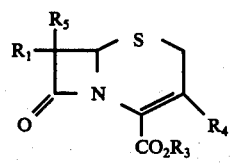

II and for the conversion of penicillins of the formula:

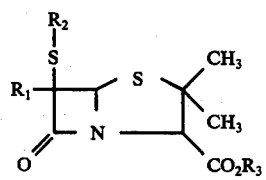

III into compounds of the formula:

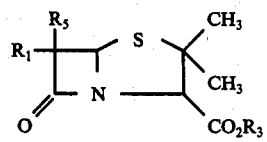

IV wherein $R_1$ phthalimido, acylamino, a Schiff base such as benzalimino, or a substituted Schiff base; $R_2$ is lower alkyl, aryl, substituted aryl, aryl lower alkyl and substituted aryl lower alkyl; $R_3$ is hydrogen, a cation such as $Na^+$, $Li^+$, $Ca^{++}$, $K^+$, $NH_4^+$ and $(C_2H_5)_3NH^+$ or a readily cleavable ester such as t-butyl, trichloroethyl, trimethylsilyl or p-methoxybenzyl; $R_4$ is methyl, acetoxymethyl or carbamoyloxy-methyl and $R_5$ is lower alkoxy, lower alkanoyloxy, aryloxy, aroyloxy, amino, lower alkylamino, di-lower alkylamino and azido, by the use of certain mercury, silver, lead, copper and thallium salts and an appropriate source of $R_5$, such as a lower alkyl alcohol, lower alkanoic acid or salt thereof, a phenol or its salt, amines, lower alkylamines, di-lower alkylamines or metal azides.

Acyl is defined in this invention as:

(a)

wherein $R^6$, $R^7$ and $R^8$ are hydrogen, lower alkyl, cycloalkyl, cycloalkenyl, cycloalkadienyl, lower alkoxy lower alkyl, thienyl, substituted thienyl, phenyl, substituted phenyl, phenoxy, substituted phenoxy, amino, nitro, halo, mercapto, lower alkylmercapto, lower alkylmercapto lower alkyl, phenylthio and substituted phenylthio wherein the substituents on the thienyl, phenyl, phenoxy, and phenylthio may be one or more of the following: lower alkyl, lower alkoxy, halo, nitro, amino and trifluoromethyl and $n$ is either 0 or an integer from 1 to 4.

(b) $R^9CO-$ wherein $R^9$ is hydrogen, amino, phenyl, substituted phenyl, lower alkoxy, thienyl, substituted thienyl, phenoxy, lower alkylthio, substituted phenoxy, β-lower alkenyl, β-lower alkylthio lower alkenyl, β-lower alkoxy lower alkenyl and β-lower alkenyloxy lower alkyl, wherein the substituents on the thienyl, phenyl and phenoxy may be one or more of the following: lower alkyl, lower alkoxy, halo, nitro, amino and trifluoromethyl.

Lower alkyl is defined as a branched or straight chain having from one to six carbon atoms. This definition also applies to terms incorporating lower alkyl with other groups, such as aryl lower alkyl which is intended to mean an aryl group linked to an alkyl group having one to six carbon atoms.

Aryl is defined as phenyl and α- and β-naphthyl.

"Substituted" as in substituted Schiff base, substituted aryl or substituted benzalimino is intended to mean unless specifically defined otherwise as mono- or disubstituted wherein said substituents may be lower alkyl, lower alkoxy, nitro, chloro, fluoro or trifluoromethyl.

Thus, the method can be represented as the conversion of a compound of the formula

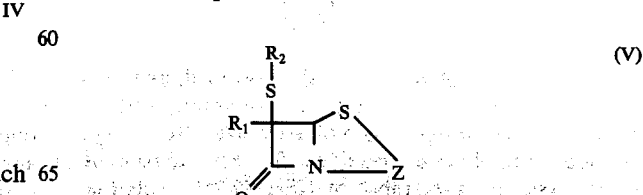

(V)

into a compound of the formula

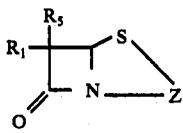 (VI)

wherein Z is

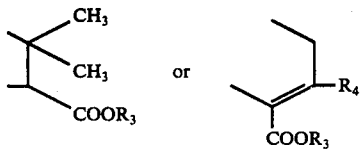

and $R_1$, $R_2$, $R_3$, $R_4$ and $R_5$ are as defined above, by the use of certain mercury, silver, lead, copper, and thallium salts and an appropriate source $R_5$, such as a lower alkyl alcohol, lower alkanoic acid or salt thereof, a phenol or its salt, amines, lower alkylamines, di-lower alkylamines or metal azides.

Numerous modifications of the naturally occurring cephalosporins have already been made in an effort to enhance antimicrobial activity with a certain degree of success being achieved. One of the positions of the cephalosporins nucleus which a number of researchers have focused upon as a place for introducing new groupings is the 7-position. Since substituents on the 7α-position tend to demonstrate higher degrees of antimicrobial activity then 7β-substituents, attempts to devise new syntheses for introducing substituents into this position are generally directed to the introduction of 7α-substituents.

This invention teaches how one may convert the readily prepared 7-arylmercapto or 7-lower alkylmercapto cephalosporin derivatives, especially 7-methylmercapto, to compounds wherein the 7-mercapto group is replaced by lower alkoxy, lower alkanoyloxy, aryloxy, azido, amino or lower alkyl amino groups.

The above described starting materials of the structure

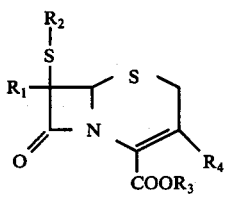

wherein $R_1$ through $R_4$ are as previously defined are converted into the compounds of this invention having the formula:

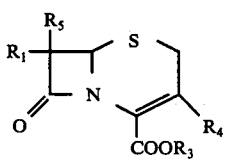

wherein $R_1$ to $R_5$ are as previously described, by the use of a reagent to supply the grouping which shall ultimately be $R_5$ in the presence of a mercury, silver, copper, lead or thallium salt catalyst. The cations to be used as catalysts are preferably in their highest oxidation state ("ic" form) and the anions are preferably one of the following: lower alkoxy, lower alkanoyloxy, cyano, nitrate, fluoro, bromo, chloro and sulfate. Mercury, silver and copper ions are the most preferred catalysts in carrying out this invention.

Also, numerous modifications of the naturally occurring pencillins have already been made in an effort to enhance antimicrobial activity with a certain degree of success being achieved. One of the positions of the pencillin nucleus which a number of researchers have focused upon as a place for introducing new groupings is the 6-position. Since substituents on the 6α-position tend to demonstrate higher degrees of antimicrobial activity than 6β-substituents, attempts to devise new syntheses for introducing substituents into this position are generally directed to the introduction of 6α-substituents.

This invention teaches how one may convert the readily prepared 6-arylmercapto or 6-lower alkylmercapto penicillin derivatives, especially 6-methylmercapto, to compounds wherein the 6-mercapto group is replaced by lower alkoxy, lower alkanyloxy, aryloxy, azido, amino, and lower alkylamino groups.

The above described starting materials of the structure

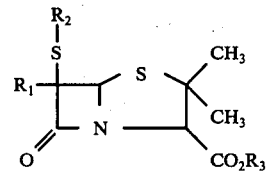

wherein $R_1$ through $R_3$ are as previously defined are converted into the compounds of this invention having the formula:

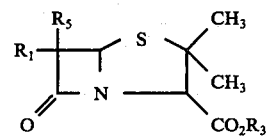

wherein $R_1$ to $R_5$ are as previously described, by the use of a reagent to supply the grouping which shall ultimately be $R_5$ in the presence of a mercury, silver, copper, lead or thallium salt catalyst. The cations to be used as catalysts are preferably in their highest oxidation state ("ic" form) and the anions are preferably one of the following: lower alkoxy, lower alkanoyloxy, cyano, nitrate, fluoro, bromo, chloro and sulfate. Mercury, silver and copper ions are the most preferred catalysts in carrying out this invention.

For $R_5$ to be lower alkoxy, the reagent may be the corresponding lower alkanol. In turn, lower alkanoyloxy is introduced by utilizing the corresponding lower alkanoic acid or a heavy metal salt thereof, (mercury, silver, etc.); aryloxy is introduced by using a phenol or its salt, azido is introduced by the use of an azide salt, such as potassium or sodium azide in the presence of catalyst; amino is introduced by the use of an excess of amine in the presence of catalyst.

The reactions of this invention are preferably conducted in inert solvents, such as dimethoxyethane, dioxane, dimethylformamide and tetramethylurea at temperatures from about −10° to about 110° C, preferably from about 0° to about 70° C. However, where a lower alkoxy group is being introduced, the corresponding alcohol may be employed as the reaction solvent. The replacement reactions of this invention take place at a relatively rapid rate so that the reaction time required is usually from about a few minutes to several hours at ambient temperature.

While this reaction is of a general nature, the preferred compounds to be prepared by the process of this invention are those of the formulas:

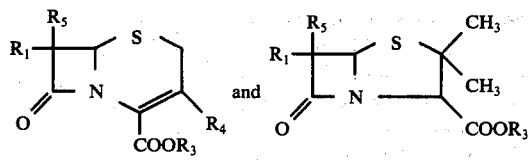

wherein $R_1$ is benzalimino, p-nitrobenzalimino, p-methoxybenzalimino, thienylacetamido, α-aminophenylacetamido, α-amino-1,4-cyclohexadienylacetamido, phenylacetamido or phenoxyacetamido, $R_4$ is methyl, acetoxymethyl or carbamoyloxymethyl and $R_5$ is lower alkoxy, lower alkanoyloxy and azido.

In addition, it has been found that if one employs a 7α-lower alkylthio- or 7α-arylthio-7-benzaliminocephalosporin, one obtains almost exclusively 7α$R_5$-substitution, whereas if a 7α-lower alkylthio- or 7α-arylthio-7-acylamino cephalosporin is employed, a mixture of 7α- and 7β-$R_5$ substituted products are obtained and that if one employs a 6α-lower alkylthio or 6α-arylthio-6-benzaliminopenicillanic acid or its ester, one obtains almost exclusively 6α$R_5$-substitution, whereas if a 6α-lower alkylthio or 6α-arylthio-6-acylamino penicillanic acid compound is employed, a mixture of 6α- and 6β-$R_5$ substituted products are obtained.

This invention is intended to encompass the preparation of both of these isomers, in addition to those which may also be encountered at other sites in the compounds of this invention.

The cephalosporins and penicillins which may be prepared by this invention are useful against gram-positive bacterial, such as *Staphylococcus aureus* and *Streptococcus pyogenes*, and especially against gram-negative bacteria such as *Escherichia coli* and *Proteus vulgaris*.

EXAMPLE 1

7α-Methylthio-7-benzaliminodesacetoxycephalosporanic Acid t-Butyl Ester(from Methylthiolation of Schiff Base)

Method A. Methyl Methanethiosulfonate Procedure

To stirred solution of 7-benzaliminodesacetoxycephalosporanic acid t-butyl ester (13.5 g, 37.7 mmol) in 200 ml dimethoxyethane at −20° under $N_2$, potassium t-butoxide (4.22 g, 37.7 mmol) is added. A deep red solution is formed which is stirred for 1.5 minutes and methyl methanethiolsulfonate (4.75 g, 37.7 mmol) is added. When the color of the solution turns from deep red to yellow, the reaction mixture is poured into pH 6.5 buffer (300 ml). The mixture is extracted with $CHCl_3$, and the $CHCl_3$ extract is washed with saturated NaCl solution, dried ($Na_2SO_4$), and evaporated to a residue. Recrystallization of the residue from acetone-hexane gives 5.38 g (35% yield) 7α-methylthio Schiff base, ir ($CHCl_3$) 1764 (β-lactam C═O ), 1715 (conjugated ester C═O), 1628 (C═N), and 1130cm⁻¹ (S-$CH_3$); pmr (DCCl₃) τ 8.45 (9H,s,t-butyl), 7.93 (3H,s,C═C-$CH_3$), 7.70 (C-6), 2.0-2.8 (5H,m,aromatics), 1.91 (1H,s,CH═N); mass spectrum, molecular ion at 404.1206 (calcd. for $C_{20}H_{24}N_2O_3S_2$:404.1226). An analytical sample that is recrystallized from $CH_2Cl_2$-pet ether melts at about 165°.

Method B. Methylsulfenyl Chloride Procedure

The procedure in part A is followed using methylsulfenyl chloride in place of methylmethanethiolsulfonate. From (20.3 g, 56.5 mmol) Schiff base, (6.33 g, 56.5 mmol) potassium t-butoxide, (4.6 g, 56.5 mmol) methylsulfenyl chloride, and 250 ml dimethoxyethane is obtained 7.70 g (34% yield) crystalline Schiff base.

EXAMPLE 2

7α-Methylthio-7-benzaliminocephalosporanic Acid t-Butyl Ester

By following the procedure in Example 1, but substituting 7-benzaliminocephalosporanic acid t-butyl ester for the Schiff base substrate, the desired product is obtained as a crystalline product having m.p. 124°–125° C.

EXAMPLE 3

7α-Phenylthio-7-(p-nitrobenzalimino)cephalosporanic Acid-p-Methoxybenzyl Ester

By following the procedure in Example 1, method B, but substituting 7(p-nitrobenzalimino)cephalosporanic acid p-methoxybenzyl ester for the Schiff base substrate and phenylsulfenyl chloride for methylsulfenyl chloride, the desired product is obtained as an amorphous product.

EXAMPLE 4

7α-Ethylthio-7-(p-methoxybenzalimino)desacetoxycephalosporanic Acid t-Butyl Ester By following the procedure in Example 1, method B, but substituting 7-(p-methoxybenzalimino)desacetoxycephalosporanic acid t-butyl ester for the Schiff base substrate and ethylsulfenyl chloride for methylsulfenyl chloride, the desired product is obtained as an amorphous material.

EXAMPLE 5

7α-Methylthio-7-phenylacetamidodesacetoxycephalosporanic Acid t-Butyl Ester

To a stirred solution of 7α-methylthio Schiff base from Example 1 (2.54 g, 6.28 mmol) in 30 ml of $CH_2Cl_2$ at room temperature under $N_2$, phenylacetyl chloride (0.84 ml, 6.28 mmol) and water (0.15 ml, 8.34 mmol) are added. The mixture is stirred for 18 hours, diluted with $CH_2Cl_2$, and poured into water. The pH is adjusted to 7.5, and the $CH_2Cl_2$ layer is washed successively with water, dilute aqueous $NaHSO_3$, and water. The $CH_2Cl_2$ solution is dried ($Na_2SO_4$) and evaporated in vacuo to a residue that crystallized from $Et_2O$-$CH_2Cl_2$ to give 1.18 g (43% yield) of the above named product: ir ($CHCl_3$) 1775 (β-lactam C═O), 1712 (conjugated C═O), 1675 (amide C═O), 1480 ("amide II" band), and 1130 cm⁻¹ (S-$CH_3$); pmr (DCCl₃) τ8.50 (9H,s,t-butyl), 7.92 (3H,s,C═C-$CH_3$), 7.75 (3H,s,-$SCH_3$), 6.82 (2H, broad singlet, C-2), 6.36 (2H, broad singlet,

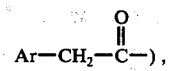

5.09 (1H,s,N-H). An analytical sample is recrystallized from $Et_2O$-$CHCl_3$ (mp 174°–175°).

EXAMPLE 6

7α-Methylthio-7-phenylacetamidocephalosporanic Acid t-Butyl Ester

By following the procedure in Example 5, but substituting 7α-methylthio-7-benzaliminocephalosporanic acid t-butyl ester for the Schiff base substrate, the desired product is obtained as an amorphous solid: pmr (DCCl₃) τ7.92 (3H,s,O-acetyl), 7.77 (3H,s,S-CH₃), 6.60 (2H, broad singlet, C-2), 6.24 (2H,s,Ar-CH₂), and 5.07 (1H,s,C-6).

EXAMPLE 7

7α-Methylthio-7-(2-thienyl)acetamidocephalosporanic Acid Trichloroethyl Ester

By following the procedure in Example 5 but substituting 7α-methylthio-7-benzaliminocephalosporanic acid trichloroethyl ester for the Schiff base and (2-thienyl)-acetyl chloride for phenylacetyl chloride, the desired product is obtained as an amorphous residue.

EXAMPLE 8

7α-Methoxy-7-phenylacetamidodesacetoxy cephalosporanic Acid t-Butyl Ester and 7β-Methoxy-7-phenylacetamidodesacetoxycephalosporanic Acid t-Butyl Ester a. To a suspension of methylthio amide from Example 5 (652 mg, 1.5 mmol) in 5 ml of refluxing CH₃OH under N₂, mercuric acetate (478 mg, 1.5 mmol) is added. The mixture is stirred under reflux for 10 minutes, cooled to room temperature and evaporated in vacuo to a residue. The residue is taken up in benzene-water, and the benzene layer is washed three times with water, dried (Na₂SO₄) and evaporated to a residue. The residue is subjected to slow fractional crystallization from small amounts of CH₃OH, which yields 420 mg pale yellow crystalline α-methoxy epimer (VIII), a residue from crystal washings, and 130 mg mother liquor whose pmr spectrum indicates a 60:40 mixture of β-methoxy and α-methoxy epimers, respectively. Slow crystallization of this mixture of epimers gives additional crystalline α-methoxy epimer and 76 mg of mother liquor whose pmr spectrum indicates a mixture of 70% β-methoxy epimer and 30% α-methoxy epimer.

The crystalline α-methoxy epimer, on recrystallization from CH₃OH, has: mp. 175°–176°; ir spectrum (CHCl₃) 1770 (β-lactam C=O), 1710 (conjugated C=O), 1960 (amide C=O), 1158, 1134, 1106, and 1086 cm⁻¹ (C-O-C and C-S-C); pmr (DCCl₃, 60 MHz), τ8.50 (9H,s,t-butyl), 7.90 (3H,s,C=C-CH₃), 6.55 (3H,s,OCH₃), 6.75, 6.95 (2H,q,J-17Hz,C-2), 6.33 (3H,s,

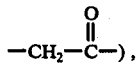

4.98 (1H,s,C-6), 3.32 (1H,b,N-H), 2.67 (5H,s,aromatics); mass spectrum molecular ion at m/e 418.1584 (calcd. for C₂₁H₂₆N₂O₅S: 418.1560).

The mother liquor containing 70% β-methoxy epimer shows: ir (CHCl₃) 1770 (β-lactam C=O), 1710 (conjugated C=O), 1690 (amide C=O), and 1155, 1138, 1100 and 1090cm⁻¹; pmr (DCCl₃) τ 8.50 (9H,s,t-butyl), 7.93 (3H,s,C=C-CH₃), 6.68 and 6.88 (2H,q,J-17Hz,C-2), 6.58 (3H,s,-OCH₃), 6.37 (2H,s, $$(2H,s,-CH_2-\overset{O}{\underset{\|}{C}}-),$$

4.83 (1H,s,C-6), 2.67 (5H,s,aromatics).

Alternatively b. To a solution of 90.5 mg. (0.33 mmole) of mercuric chloride in 2 ml. of anhydrous methanol is added 36 mg. (0.66 mmole) of sodium methoxide. An orange precipitate forms immediately. To this mixture is added 109 mg. (0.33 mmole) of 7α-methylthio compound from example 5. The mixture is stirred under nitrogen for 30 minutes at room temperature. The methanol is removed under reduced pressure, and the residue is taken up in benzene and water. The benzene layer is washed twice with water, dried (Na₂SO₄), and evaporated to give 104 mg. of 7α-methoxy-7-phenylacetamidodesacetoxycephalosporanic acid t-butyl ester which crystallizes on standing at room temperature.

EXAMPLE 9

7-Methoxy-7-phenylacetamidocephalosporanic Acid t-Butyl Esters (7α-Methoxy and 7β-Methoxy Epimeric Mixture)

To a suspension of 1.5 mmole of 7α-methylthio-7-phenylacetamidocephalosporanic acid t-butyl ester in 5 ml of methanol is added 1.5 mmole of mercuric acetate. The mixture is stirred under nitrogen for 30 minutes, and the solvent is removed under reduced pressure. The residue is taken up in benzene and water, and the benzene layer is washed with dilute sodium bicarbonate solution and water, dried (Na₂SO₄), and evaporated to give the desired product as an amorphous residue.

EXAMPLE 10

Sodium Salts of 7α-Methoxy-7-propionamidodesacetoxycephalosporanic Acid and 7β-Methoxy-7-propionamidodesacetoxycephalosporanic Acid The procedure described in Example 9 is used to solvolyze the sodium salt of 7α-methylthio-7-propionamidodesacetoxycephalosporanic acid. However, the workup is modified such that the residue from the reaction mixture is taken up in water and, after adjusting the acidity of the aqueous solution to pH 2.5, the aqueous solution is exhaustively extracted with methylene chloride. The combined extracts are dried (Na₂SO₄) and solvent is removed under reduced pressure. The residue is suspended in methanol and one equivalent of sodium methoxide is added while stirring vigorously. Removal of solvent in vacuo yields a mixture of the desired sodium salts as an amorphous solid.

EXAMPLE 11

7α-Methoxy-7-phenylacetamidocephalosporanic Acid and 7β-Methoxy-7-phenylacetamidocephalosporanic Acid The procedure described in Example 9 is used to solvolyze 7α-methylthio-7-phenylacetamidocephalosporanic acid. However, the workup is modified such that the residue, after removal of methanol from the reaction mixture is extracted with methylene chloride and filtered to remove insoluble material.

The filtrate is washed with water, dried (Na₂SO₄), and solvent removed in vacuo yields the desired products as an amorphous residue containing the 7α- and 7β-methoxy isomers.

EXAMPLE 12

7α-Methoxy-7-phenylacetamidodesacetoxycephalosporanic Acid t-Butyl Ester

Silver tetrafluoroborate (59 mg, 0.30 mmol) is added to a suspension of methylthio amide (Example 5) (60 mg, 0.15 mmol) in anhydrous methanol (1 ml) at room temperature. After stirring for 45 minutes, the mixture is diluted with anhydrous ether, filtered through Celite, and washed successively with 5% sodium bicarbonate solution, sodium chloride solution, and water. The ethereal solution is dried ($Na_2SO_4$) and removal of solvent yields a solid identical with the 7α-methoxy amide prepared by the method described in Example 8.

EXAMPLE 13

7α-Acetoxy-7-phenylacetamidodesacetoxycephalosporanic Acid t-Butyl Ester a. To a suspension of the 7α-methylthio ester (Example 5) (651 mg, 1.5 mmol) in 5 ml of dimethoxyethane is added mercuric acetate (478.5 mg, 1.5 mmol). The mixture is stirred under nitrogen for 20 minutes at room temperature. The precipitate is filtered and washed with dimethoxyethane yielding 413 mg pale yellow powder. The filtrate is evaporated to a residue that is taken up in benzene-water. The benzene layer is washed with water, dried ($Na_2SO_4$) and evaporated to give 620 mg (93% yield) of the above named 7α-acetoxy t-butyl ester as an almost colorless oil: ir ($CHCl_3$) 1785 (β-lactam C=O), 1750(sh) (ester C=O), 1720-1685 (broad band, conjugated C=O and amide C=O), and 1480cm$^{-1}$ (amide IIband); pmr ($DCCl_3$) τ8.48 (9H,s,t-butyl), 7.90

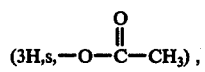

(3H,s,—O—C(=O)—CH$_3$), 6.98 (2H,s,C-2), 6.32

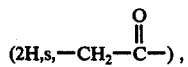

(2H,s,—CH$_2$—C(=O)—), 4.87 (1H,s,C-6), 2.85 (1H,s,N-H), 2.67 (5H,s,aromatics); mass spectrum, no molecular ion but m/e 344 (M-CH$_3$COOH).

Alternatively b. To 109 mg (0.25 mmole) of methylthio amide (Example 5) in 2 ml of acetic acid is added 164 mg (2 mmoles) of sodium acetate, followed by 80 mg (0.25 mmole) of mercuric acetate. The mixture is stirred for 15 minutes at room temperature, and the acetic acid is removed in vacuo. The residue is taken up in benzene and water. The benzene layer is washed with aqueous sodium chloride solution, dried ($Na_2SO_4$), and evaporated to give 112 mg of 7α-acetoxy-7-phenylacetamidodesacetoxycephalosporanic acid t-butyl ester as a residue.

EXAMPLE 14

7α-Acetoxy- and 7β-acetoxy-phenylacetamidodesacetoxycephalosporanic Acid t-Butyl Esters A mixture of 63 mg (0.14 mmole) of 7α-acetoxy compound and 45 mg (0.14 mmole) of mercuric acetate in 0.5 ml of dimethylformamide is stirred under nitrogen at room temperature for 25 minutes. The mixture is taken up in water and benzene, and the benzene layer is washed twice with water, dried ($Na_2SO_4$), and evaporated in vacuo to give 58 mg of yellow residue consisting of approximately equal quantities of 7α-acetoxy-7-phenylacetamidodesacetoxycephalosporanic acid t-butyl ester and 7β-acetoxy-7-phenylacetamidodesacetoxycephalosporanic acid t-butyl ester.

EXAMPLE 15

7-Benzalimino-7α-methoxydesacetoxycephalosporanic Acid t-Butyl Ester

A mixture of mercuric acetate (431 mg, 0.135 mmol) and the methylthio Schiff base from Example 1 (500 mg, 0.124 mmol) in anhydrous methanol (15 ml) is stirred at room temperature for 1 hour. Dilution with anhydrous ether (75 ml) and filtration through Celite removes insoluble material. After stripping solvent under reduced pressure, the residue is taken up in ether and washed with 5% bicarbonate solution and water. The organic layer is treated with Norite, and the volume of solvent is reduced, yielding the above named product as colorless crystals, 305 mg, mp 141°–142°. A second crop is obtained from the filtrate, 520 mg, mp 137.5°–139° (total yield 74%). Recrystallization from methanol yields analytically pure material: mp 142°–143°; ir ($CHCl_3$) 1770 (β-lactam C=O), 1715 (t-butyl ester C=O), 1635cm$^{-1}$ (C=N); pmr ($DCCl_3$) τ8.47 (9H,s,t-butyl CH$_3$), 7.78 (3H,s,CH$_3$), 6.98 (1H,d,J$_{gem}$=17Hz,C-2), 6.55 (1H,d,J$_{gem}$=17Hz,C-2), 6.39 (3H,s,OCH$_3$), 4.92 (1H,s,C-6), 1.97-2.75 (5H, complex m, aromatic), 1.30 (1H,s,azomethine CH).

Anal. Calcd for $C_{20}H_{24}N_2O_4S$: C, 61.84; H, 6.23; N, 7.21; Found: C, 61.60; H, 6.18; N, 7.24.

EXAMPLE 16

7-Benzalimino-7α-ethoxydesacetoxycephalosporanic Acid t-Butyl Ester

The procedure described in Example 15 is used to prepare the above named compound. The methylthio Schiff base from Example 1 is solvolyzed in absolute ethanol and catalyzed by the addition of 1.1 equivalents of mercuric acetate. After the workup, the 7α-ethoxy Schiff base is obtained:

pmr ($DCCl_3$) τ8.70 (3H,t,OCH$_2$CH$_3$), 8.42 (9H,s,t-butyl CH$_3$), 7.93 (3H,s,CH$_3$), 6.73 (2H,dd,C-2), 6.10 (2H,q,OCH$_2$CH$_3$),4.92 (1H,s,C-6), 1.95-2.67 (5H, complex m, aromatic; M+, m/e 402 ($C_{21}H_{26}N_2O_4S$ = 402).

EXAMPLE 17

General Procedure for the metal catalyzed solvolysis of the 7α-alkylthio or 7α-arylthio cephems (I) shown in Table I.

To a solution of the 7α-alkylthio or 7α-arylthio cephem (I) in the indicated anhydrous solvent system, is added 1.0 equivalent of metal catalyst. The heterogenous mixture is stirred, preferably under an inert atmosphere, at the temperature shown in Table I. The reaction is best followed to completion by monitoring the mixture on thin layer chromatography since reaction times are found to vary. After removal of the solvent system in vacuo, the residue is diluted with an organic solvent, which is immiscible with water, and filtered to remove insoluble materials. The solution is washed with water and the organic layer is dried and evaporated under reduced pressure. An amorphous residue is obtained containing the appropriate cephem derivative indicated in Table I.

Table I

| R₁ | R₂ | R₃ | R₄ | R₅ | Catalyst | Solvent | Temp. |
|---|---|---|---|---|---|---|---|
| φ-CH$_2$-CONH | CH$_3$ | H | CH$_3$ | CH$_3$O(α+β) | Hg(OAc)$_2$ | CH$_3$OH | 60° |
| φ-O-CH$_2$-CONH | CH$_3$ | H | -CH$_2$OAc | C$_6$H$_5$COO(α+β) | Hg(OAc)$_2$ | C$_6$H$_5$CooNa-DMF | 40° |
| (2-thienyl)-CH$_2$-CO-NH | CH$_3$ | CH$_2$-CCl$_3$ | CH$_2$OAc | CH$_3$O(α+β) | Hg(OAc)$_2$ | CH$_3$OH | 25° |
| Ph-CH(CONH)-NH-C(CH$_3$)=CH-COOCH$_3$ | CH$_3$ | CH$_2$-CCl$_3$ | CH$_2$OAc | CH$_3$O(α+β) | Hg(OAc)$_2$ | CH$_3$OH | 25° |
| Ph-CH(CONH)-NH$_2$ | CH$_3$ | p-CH$_3$O-C$_6$H$_4$-CH$_2$- | CH$_2$OAc | CH$_3$O(α+β) | Hg(OAc)$_2$ | CH$_3$OH | 25° |
| Ph-S-CH$_2$-CONH | CH$_3$CH$_2$ | t-butyl | CH$_3$ | CH$_3$O(α+β) | Hg(OAc)$_2$ | CH$_3$OH | 25° |
| cyclohexyl-CONH | CH$_3$ | p-CH$_3$O-C$_6$H$_4$-CH$_2$- | CH$_3$ | CH$_3$O(α+β) | Hg(OAc)$_2$ | CH$_3$OH | 25° |
| (2-furyl)-CH$_2$-O-CH$_2$-CONH | CH$_3$CH$_2$ | t-butyl | CH$_3$ | CH$_3$O(α+β) | Hg(OAc)$_2$ | CH$_3$OH | 25° |
| (2-ethylphenyl)-C(=O)-N(CH$_2$-O-)- | CH$_3$ | t-butyl | CH$_3$ | CH$_3$O(α+β) | Hg(OAc)$_2$ | CH$_3$OH | 25° |
| Ph-CH$_2$CONH | CH$_3$ | t-butyl | CH$_3$ | N$_3$(α+β) | Hg(OAc)$_2$ | NaN$_3$ in DMF | 25° |
| (2-thienyl)-CH$_2$CONH | CH$_3$ | t-butyl | CH$_3$ | N$_3$(α+β) | Hg(OAc)$_2$ | NaN$_3$ in TMU* | 25° |

Table I-continued

| R$_1$ | R$_2$ | R$_3$ | R$_4$ | R$_5$ | Catalyst | Solvent | Temp. |
|---|---|---|---|---|---|---|---|
| PhCH$_2$—CONH | CH$_3$ | t-butyl | CH$_3$ | CH$_3$CH$_2$O (α+β) | Hg(OAc)$_2$ | CH$_3$OH | 25° |
| (thienyl-2)CH$_2$—CONH | CH$_3$ | 4-CH$_3$O-C$_6$H$_4$-CH$_2$ | CH$_2$OCONH$_2$ | CH$_3$CH$_2$O (α+β) | Hg(OAc)$_2$ | CH$_3$CH$_2$OH | 60° |
| PhCH$_2$—CONH | CH$_3$ | t-butyl | CH$_3$ | CH$_3$CO$_2$ (α) | Hg(OAc)$_2$ | THF | 25° |
| (thienyl-2)CH$_2$—CONH | CH$_3$ | t-butyl | CH$_2$OAc | CH$_3$CO$_2$ (α) | Hg(OAc)$_2$ | DME | 25° |
| PhCH(NH$_2$)—CONH | CH$_3$ | CH$_3$ | CH$_3$ | CH$_3$CO$_2$ (α) | Hg(OAc)$_2$ | Dioxane-HOAc | 25° |
| PhCH$_2$—CONH | C$_6$H$_5$ | t-butyl | CH$_3$ | CH$_3$O (α+β) | Hg(OAc)$_2$ | CH$_3$OH | 25° |
| PhCH$_2$—CONH | CH$_3$ | t-butyl | CH$_3$ | CH$_3$O (α) | Hg(OMe)$_2$ | CH$_3$OH | 25° |
| PhCH$_2$—CONH | CH$_3$ | t-butyl | CH$_2$OAc | CH$_3$CO$_2$ (α) | Tl(OAc)$_3$ | DME—HOAc | 25° |
| (thienyl-2)CH$_2$—CONH | CH$_3$ | 4-CH$_3$O-C$_6$H$_4$-CH$_2$ | CH$_2$OAc | CH$_3$CO$_2$ (α) | Tl(OAc)$_3$ | Dioxane-HOAc | 25° |
| PhCH$_2$—CONH | CH$_3$ | t-butyl | CH$_3$ | CH$_3$O (α) | AgBF$_4$ | CH$_3$OH | 25° |

Table I-continued

| R₁ | R₂ | R₃ | R₄ | R₅ | Catalyst | Solvent | Temp. |
|---|---|---|---|---|---|---|---|
| Ph-CH₂CONH- | CH₃ | t-butyl | CH₃ | (CH₃)₂N—(α+β) | Hg(OAc)₂ | (CH₃)₂NH/DMF | 25° |
| (2-thienyl)-CH₂-CONH- | CH₃CH₂ | t-butyl | CH₂OAc | CH₃O (α) | AgBF₄ | CH₃OH | 25° |
| 2,6-dimethoxyphenyl-CONH- (with 4-CH₃O-C₆H₄-CH₂ group) | CH₃ | t-butyl | CH₃ | CH₃CH₂O (α) | AgBF₄ | CH₃CH₂OH | Reflux |
| Ph-O-CH₂-CONH- | CH₃ | t-butyl | CH₃ | CH₃O (α) | AgClO₄ | CH₃OH | 25° |
| Ph-CH(NH-C(CH₃)=CH-CO-OCH₃)-CONH- | CH₃ | CH₃ | CH₃ | CH₃O (α) | AgNO₃ | CH₃OH | 25° |
| Ph-CH(NH₂)-CONH- | CH₃ | t-butyl | CH₂OAc | CH₃CO₂ (α+β) | AgOAc | HOAc | 25° |
| Ph-CH₂-CONH- | CH₃ | t-butyl | CH₃ | CH₃CO₂ (α+β) | Pb(OAc)₄ | DME—HOAc | 25° |
| Ph-CH=N- | CH₃ | t-butyl | CH₃ | CH₃O (α) | Hg(OAc)₂ | CH₃OH | 25° |
| Ph-CH=N- | CH₃ | t-butyl | CH₃ | CH₃CH₂O (α) | Hg(OAc)₂ | CH₃CH₂OH | Reflux |

Table I-continued

| $R_1$ | $R_2$ | $R_3$ | $R_4$ | $R_5$ | Catalyst | Solvent | Temp. |
|---|---|---|---|---|---|---|---|
| 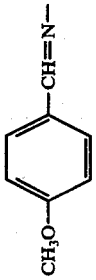 | $CH_3CH_2$ | t-butyl | $CH_3$ | $CH_3O\ (\alpha)$ | $Hg(OAc)_2$ | $CH_3OH$ | 25° |
| 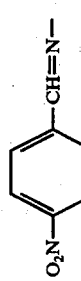 |  | t-butyl | $CH_2OAc$ | $CH_3CH_2O\ (\alpha)$ | $Hg(OAc)_2$ | $CH_3CH_2OH$ | Reflux |
|  | $CH_3$ | t-butyl | $CH_3$ | $AcO\ (\alpha)$ | $Hg(OAc)_2$ | DME | 25° |
| 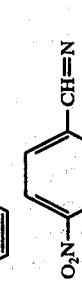 | $CH_3$ | t-butyl | $CH_3$ | $N_3\ (\alpha)$ | $Hg(OAc)_2$ | $NaN_3$ in DMF | 25° |
| 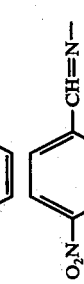 | $CH_3$ | t-butyl | $CH_3$ | $N_3\ (\alpha)$ | $AgBF_4$ | $NaN_3$ in DMF | 25° |
| 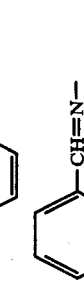 | $CH_3$ | 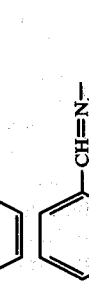 | $CH_3$ | $AcO\ (\alpha)$ | $Hg(OAc)_2$ | Dioxane | 25° |
| 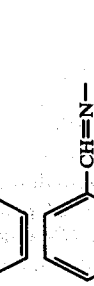 | $CH_3$ | t-butyl | $CH_2OAc$ | $CH_3O\ (\alpha)$ | $AgBF_4$ | $CH_3OH$ | 25° |
|  | $CH_3$ | t-butyl | $CH_3$ | $AcO\ (\alpha)$ | $Tl(OAc)_3$ | DME | 25° |
|  | $CH_3$ | t-butyl | $CH_3$ | $(CH_3)_2N-(\alpha)$ | $Hg(OAc)_2$ | $(CH_3)_2NH/DMF$ | 25° |

*TMU = Tetramethylurea

EXAMPLES

EXAMPLE 18

6α-Methylthio-6-benzaliminopenicillanic Acid p-Methoxybenzyl Ester

Method A. To a stirred solution of 6-benzaliminopenicillanic acid p-methoxybenzyl ester (1.04 g, 2.43 mmol) in dimethoxyethane (150 ml) at −10° is added potassium t-butoxide (272 mg, 2.43 mmol). The orange solution is stirred for 2 minutes, and methyl methanethiolsulfonate (306 mg, 2.43 mmol) is added. After stirring for 1 hour at −10°, the mixture is poured into pH 6.6 buffer (300 ml) and extracted with ethyl acetate. Evaporation of the dried (MgSO$_4$) extract gives 1.10 g of desired product as a yellow oil. The oil has: ir (CHCl$_3$) 1765 (β-lactam C=O), 1740 (ester C=O), and 1610cm$^{-1}$ (C=N); pmr (DCCl$_3$)τ8.67 (3H,s,-CH$_3$), 8.57 (3H,s,-CH$_3$), 7.83 (3H,s,-SCH$_3$), 6.37 (3H,s,-OCH$_3$), 5.57 (1H,s,C-3), 4.93 (2H,s,-OCH$_2$), 4.43 (1H,s,C-5), 2.93 (9H,m,aromatic), and 1.33 (1H,s,CH=N); mass spectrum molecular ion at m/e 470, base peak at m/e 121.
Method B. Methylsulfenyl Chloride Procedure The procedure in part A is followed using 2.43 mmol of methylsulfenyl chloride in place of methylmethanethiolsulfonate.

EXAMPLE 19

6α-Methylthio-6-benzaliminopenicillanic Acid Methyl Ester

By following the procedure in Example 18, but substituting 6-benzaliminopenicillanic acid methyl ester for the Schiff base substrate, the desired product is obtained.

EXAMPLE 20

6α-Phenylthio-6-(p-nitrobenzalimino)penicillanic Acid p-Methoxybenzyl Ester

By following the procedure in Example 18, method B, but substituting 6(p-nitrobenzalimino)penicillanic acid p-methoxybenzyl ester for the Schiff base substrate and phenylsulfenyl chloride for methylsulfenyl chloride, the desired product is obtained.

EXAMPLE 21

6α-Ethylthio-6-(p-methoxybenzalimino)penicillanic Acid p-Methoxybenzyl Ester

By following the procedure in Example 18, method B, but substituting 6-(p-methoxybenzalimino)penicillanic acid p-methoxybenzyl ester for the Schiff base substrate and ethylsulfenyl chloride for methylsulfenyl chloride, the desired product is obtained.

EXAMPLE 22

6α-Methylthio-6-phenoxyacetamidopenicillanic Acid p-Methoxybenzyl Ester

To a solution of methylthio Schiff base from Example 18 (104 mg, 2.45 mmol) in 4 ml of dimethoxyethane is added phenoxyacetyl chloride (33.5 ml, 2.45 mmol), followed by water (4 ml, 2.45 mmol). The mixture is stirred for 40 min at room temperature and poured into water. Extraction with ethyl acetate gives a yellow oil (61 mg) that is purified by tlc on Quantum PQIF silica gel in the system, hexane-ethyl acetate (4:1), to give 32 mg (25% yield) of desired product as a colorless oil with: ir (CHCl$_3$ 1780 (β-lactam C=O), 1745 (ester C=O), and 1692 (amide C=O); pmr (DCCl$_3$)τ8.67 (3H,s,-CH$_3$), 8.53 (3H,s,-CH$_3$), 7.73 (3H,s,-SCH$_3$), 6.20 (3H,s,-OCH$_3$), 5.63 (1H,s,C-3), 5.50 (2H,s,-CH$_2$C=O), 4.90 (2H,s,-OCH$_2$), 4.45 (1H,s,C-5), 3.00 (9H,s, aromatic), and 1.93 (1H,m,N-H).

The desired product is also prepared in 20% yield by treating the methylthio Schiff base from Example 18 with equivalent amounts of p-toluenesulfonic acid monohydrate, triethylamine, and phenoxyacetyl chloride in EtOAc.

EXAMPLE 23

6 α-Methylthio-6-phenylacetamidopenicillanic Acid p-Methoxybenzyl Ester

The 6α-methylthio amide is obtained in 14% yield by the procedure described for the preparation of amide in Example 22, but substituting phenylacetylchloride for phenoxyacetyl chloride. It has: ir (CHCl$_3$) 1775 (β-lactam C=O), 1740 (ester C=O), and 1680cm$^{-3}$ (amide C=O); pmr (DCCl$_3$)τ8.70 (3H,s,-CH$_3$), 7.83 (3H,s,-SCH$_3$),

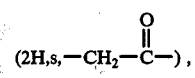

(2H,s,—CH$_2$—C—), 6.18 (3H,s,-OCH$_3$), 5.63 (1H,s, C-2), 4.88 (2H,s,-OCH$_2$), 4.45 (1H,s,C-5), and 3.30-2.57 (10H, m,N-H and aromatics).

EXAMPLE 24

6α-Methylthio-6-(2-thienyl)acetamidopenicillanic Acid Trichloroethyl Ester

By following the procedure in Example 22 but substituting 6α-methylthio-6-benzaliminopenicillanic acid trichloroethyl ester for the Schiff base and (2-thienyl)-acetyl chloride for phenoxyacetyl chloride, the desired product is obtained as an amorphous residue.

EXAMPLE 25

6α-Methoxy-6-phenylacetamidopenicillanic acid p-methoxybenzyl ester and
6β-Methoxy-6-phenylacetamidopenicillanic acid p-methoxybenzyl ester a. To a suspension of methylthio amide from Example 23 (1.5 mmol.) in 5 ml. of refluxing CH$_3$OH under N$_2$, mercuric acetate (1.5 mmol.) is added. The mixture is stirred under reflux for 10 minutes, cooled to room temperature and evaporated in vacuo to a residue. The residue is taken up in benzene-water, and the benzene layer is washed three times with water, dried (Na$_2$SO$_4$) and evaporated to a residue. The residue consists of a mixture of 6α- and 6β-methoxy epimers. Alternatively:

b. To a solution of 90.5 mg. (0.33 mmole) of mercuric chloride in 2 ml. of anhydrous methanol is added 36 mg. (0.66 mmole) of sodium methoxide. An orange precipitate forms immediately. To this mixture is added (0.33 mmole) of 6α-methylthio compound from Example 23. The mixture is stirred under nitrogen for 30 minutes at room temperature. The methanol is removed under reduced pressure, and the residue is taken up in benzene and water. The benzene layer is washed twice with water, dried (Na$_2$SO$_4$), and evaporated to give the 6β-methoxy-6-phenylacetamidopenicillanic acid p-methoxybenzyl ester.

EXAMPLE 26

6-Methoxy-6-phenylacetamidopenicillanic acid p-methoxybenzyl esters (6α-methoxy or 6β-methoxy epimeric mixture)

To a suspension of 1.5 mmole of 6α-methylthio-6-phenylacetamidopenicillanic acid t-butyl ester in 5 ml. of methanol is added 1.5 mmole of mercuric acetate. The mixture is stirred under nitrogen for 30 minutes, and the solvent is removed under reduced pressure. The residue is taken up in benzene and water, and the benzene layer is washed with dilute sodium bicarbonate solution and water, dried ($Na_2SO_4$), and evaporated to give the desired product as an amorphous residue.

EXAMPLE 27

Sodium Salts of 6α-Methoxy-6-propionamidopenicillanic Acid and 6β-Methoxy-6-propionamidopenicillanic Acid The procedure described in Example 26 is used to solvolyze the sodium salt of 6α-methylthio-6-propionamidopenicillanic acid. However, the workup is modified such that the residue from the reaction mixture is taken up in water and, after adjusting the acidity of the aqueous solution to pH 3.5, the aqueous solution is exhaustively extracted with methylene chloride. The combined extracts are dried ($Na_2SO_4$) and solvent is removed under reduced pressure. The residue is suspended in methanol and one equivalent of sodium methoxide is added while stirring vigorously. Removal of solvent in vacuo yields a mixture of the desired sodium salts as an amorphous solid.

EXAMPLE 11

6α-Methoxy-6-phenylacetamido and 6β-Methoxy-6-phenylacetamidopenicillanic Acid

The procedure described in Example 26 is used to solvolyze 6α-methylthio-6-phenylacetamidopenicillanic. However, the workup is modified such that the residue, after removal of methanol from the reaction mixture, is extracted with methylene chloride and filtered to remove insoluble material.

The filtrate is washed with water, dried ($Na_2SO_4$), and solvent removed in vacuo yields the desired products as an amorphous residue containing the 6α- and 6β-methoxy isomers.

EXAMPLE 29

6α-Methoxy-6-phenylacetamidopenicillanic acid p-methoxybenzyl ester

Silver tetrafluoroborate (59 mg., 0.30 mmol.) is added to a suspension of methylthio amide (Example 23) (60 mg., 0.15 mmol.) in anhydrous methanol (1 ml.) at room temperature. After stirring for 45 minutes, the mixture is diluted with anhydrous ether, filtered through Celite, and washed successively with 5% sodium bicarbonate solution, sodium chloride solution, and water. The ethereal solution is dried ($Na_2SO_4$), and removal of solvent yields a solid identical with the 6α-methoxy amide prepared by the method described in Example 25.

EXAMPLE 30

6α-Acetoxy-6-phenylacetamidopenicillanic acid p-methoxybenzyl ester a. To a suspension of the 6α-methylthio ester (Example 23) (1.5 mmol.) in 5 ml. of dimethoxyethane is added mercuric acetate (1.5 mmol.). The mixture is stirred under nitrogen for 20 minutes at room temperature. The precipitate is filtered and washed with dimethoxyethane yielding 413 mg. pale yellow powder. The filtrate is evaporated to a residue that is taken up in benzene-water. The benzene layer is washed with water, dried ($Na_2SO_4$) and evaporated to give the above named ester. Alternatively:

b. To 0.25 mmole of methylthio amide (Example 23) in 2 ml. of acetic acid is added 2 mmoles of sodium acetate, followed by 0.25 mmole of mercuric acetate. The mixture is stirred for 15 minutes at room temperature, and the acetic acid is removed in vacuo. The residue is taken up in benzene and water. The benzene layer is washed with aqueous sodium chloride solution, dried ($Na_2SO_4$), and evaporated to give the ester as a residue.

EXAMPLE 31

6α-Methylthio-6-benzaliminopenicillanic Acid and 6α-Methylthio-6-aminopenicillanic Acid To a slurry of 6-benzaliminopenicillanic acid (5.11 g, 16.9 mmol) in dry dimethoxyethane (200 ml) at room temperature is added potassium t-butoxide (1.89 g, 16.9 mmol). The mixture turns orange, and complete solution occurrs after 3 minutes Trimethylsilyl chloride (1.83 g, 16.9 mmol) is added, and the mixture is stirred for 12 minutes as it cools to −10°. Potassium t-butoxide (1.89 g, 16.9 mmol) is added, and the solution turns red. After 15 minutes, methyl methanethiosulfonate (2.12 g, 16.9 mmol) is added, and stirring is continued for 30 minutes at −10°. The dimethoxyethane is removed in vacuo, and the residue is taken up in pH 6.8 phosphate buffer and EtOAc. The EtOAc layer is discarded, and the aqueous layer is washed repeatedly with EtOAc. The EtOAc washings are discarded, and the aqueous part is layered with EtOAc and adjusted to pH 4.0 with dilute HCl. Extraction with $CHCl_3$ and EtOAc gives a residue, after drying ($MgSO_4$) and concentration. Trituration of the residue with $CHCl_3$ gives 240 mg of 6-α-methylthio-6-aminopenicillanic acid as a solid and a supernate. Evaporation of the supernate gives 650 mg of 6-α-methylthio-6-benzylimino penicillanic acid (19% yield) as an oil.

Adjustment of the pH 4 aqueous solution to pH 1.9 and extraction with EtOAc gives a further quantity of the amino acid (800 mg), for a total yield of 23%.

The amorphous amino acid has: ir (Nujol) 1755 (β-lactam C=O), and 1715cm⁻¹ (acid C=O); mp 172°–176° (dec); pmr (DMSO-d₆) τ8.60 (3H,s,-CH₃), 8.53 (3H,s,-CH₃), 7.85 (3H,s,-SCH₃), 5.82 (1H,s,C-5), and 3.90 (3H,broad,NH₃+) mass spectrum, molecular ion m/e 262, base peak m/e 160. Anal. Calcd. for $C_9H_{14}N_2O_3S_2$: C,41.22; H,5.38; N,10.68. Found: C,41.88; H,5.78; N,10.00.

The Schiff base has: ir ($CHCl_3$) 1760 (β-lactam C=O), 1720 (COOH), and 1622 cm⁻¹ (C=N); pmr ($DCCl_3$) τ8.43 (6H,s,2-CH₃), 7.73 (3H,s,SCH₃), 5.60 (1H,s,C-3), 4.45 (1H,s,C-5), 4.60 (5H, m, aromatics), 1.57 (1H,broad,COOH); mass spectrum of trimethylsilyl ester, molecular ion at m/e 422.

EXAMPLE 32

6α-Methylthio-6-phenoxyacetamidopenicillanic Acid

To a stirred suspension of the methylthio amino acid from Example 31 (127 mg, 0.485 mmol) in dimethoxyethane (12 ml) is added, N,O-bis-trimethylsilylacetamide (100 ml, 0.485 mmol). Solution occurs after 15 minutes of stirring. Triethylamine (68 ml, 0.485 mmol) and phenoxyacetyl chloride (67 ml, 0.485 mmol) are added sequentially, and the mixture is stirred for 1.5 hour at room temperature and concentrated under vacuum to a residue. The residue is taken up in EtOAc-H₂O, and the water layer is discarded. Water is added to the EtOAc layer, and the pH is adjusted to 7.5. The EtOAc layer is discarded, and the aqueous solution is covered with EtOAc and adjusted to pH 3.2 with dilute HCl. The resulting EtOAc extract is dried (Na₂SO₄) and evaporated to a residue. Trituration with hexane-benzene gives 72 mg of amorphous product (38% yield); ir (CHCl₃) 1780 (β-lactam C=O), 1730 (COOH), and 1690cm⁻¹ (amide C=O) pmr (DCCl₃) τ8.47 (6H,s,2CH₃), 7.70 (3H,s,-SCH₃), 5.50 (1H,s,C-3), 5.33 (2H,s,O-CH₂), 4.25 (1H,s,C-5), 2.83 (5H,m,aromatics), and 2.30 (1H,s,N-H) mass spectrum of trimethylsilyl ester, molecular ion at m/e 468.

EXAMPLE 33

6α-Methylthio-6-phenylacetamidopenicillanic Acid

This acid is obtained in 78% yield by the method described for the preparation of the acid of the previous example, but by substituting phenylacetyl chloride in place of phenoxyacetyl chloride. The amorphous acid has: ir (CHCl₃) 1777 (β-lactam C=O), 1725 (COOH), and 1680cm⁻¹ (amide C=O) pmr (DCCl₃) τ8.57 (6H,m,2CH₃), 7.83 (3H,s,-SCH₃), 6.38 (2H,s,

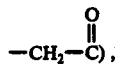

5.67 (1H,s,C-3), 4.48 (1H,s,C-5), 2.67 (5H,m,aromatics), 2.17 (1H,m,N-H); mass spectrum of trimethylsilyl ester, molecular ion at m/e 452.

EXAMPLE 34

6α-Acetoxy- and 6β-acetoxy-phenylacetamidopenicillanic Acid p-Methoxylbenzyl Ester A mixture of 0.14 mmole of 6α-acetoxy compound from Example 30 and 0.14 mmole of mercuric acetate in 0.5 ml of dimethylformamide is stirred under nitrogen at room temperature for 25 minutes. The mixture is taken up in water and benzene, and the benzene layer is washed twice with water, dried (Na₂SO₄), and evaporated in vacuo to give a residue consisting of approximately equal quantities of the 6-α and 6-β acetoxy epimers.

EXAMPLE 35

6-Benzalimino-6α-methoxypenicillanic Acid, p-Methoxybenzyl Ester

A mixture of mercuric acetate (0.135 mmol) and the methylthio Schiff base from Example 18 (0.124 mmol) in anhydrous methanol (15 ml) is stirred at room temperature for one hour. Dilution with anhydrous ether (75 ml) and filtration through Celite removes insoluble material. After stripping solvent under reduced pressure, the residue is taken up in ether and washed with 5% bicarbonate solution and water. The organic layer is treated with Norite, and the volume of solvent is reduced, yielding the above named product as a residue.

EXAMPLE 36

6-Benzalimino-6α-ethoxypenicillanic Acid p-Methoxybenzyl Ester

The procedure described in Example 35 is used to prepare the above named compound. The methylthio Schiff base from Example 18 is solvolyzed in absolute ethanol and catalyzed by the addition of 1.1 equivalents of mercuric acetate. After the workup, the desired 6α-ethoxy Schiff base is obtained.

EXAMPLE 37

General Procedure for the metal catalyzed solvolysis of the 6α-alkylthio or 6α-arylthio penams (I) shown in Table II.

To a stirred solution of the 6α-alkylthio or 6α-arylthio penam (I) in the indicated anhydrous solvent system, is added 1.0 equivalent of metal catalyst. The heterogenous mixture is stirred, preferably under an inert atmosphere, at the temperature shown in Table II. The reaction is best followed to completion by monitoring the mixture on thin layer chromatography since reaction times are found to vary. After removal of the solvent system in vacuo, the residue is diluted with an organic solvent, which is immiscible with water, and filtered to remove insoluble materials. The solution is washed with water and the organic layer is dried and evaporated under reduced pressure. An amorphous residue is obtained containing the appropriate penam derivative indicated in Table II.

TABLE II

| R₁ | R₂ | R₃ | R₅ | Catalyst | Solvent | Temp. |
|---|---|---|---|---|---|---|
| φ—CH₂—CONH | CH₃ | H | CH₃O(α+β) | Hg(OAc)₂ | CH₃OH | 60° |
| φ—O—CH₂—CONH | CH₃ | H | C₆H₅COO (α+β) | Hg(OAc)₂ | C₆H₅COONa, DMF | 40° |
| ⟨S⟩—CH₂—CO—NH | CH₃ | CH₂—CCl₃ | CH₃O(α+β) | Hg(OAc)₂ | CH₃OH | 25° |
| φ—CH—CONH, NH, C(OCH₃)=CH | CH₃ | CH₂—CCl₃ | CH₃O(α+β) | Hg(OAc)₂ | CH₃OH | 25° |
| φ—CH(NH₂)—CONH | CH₃ | CH₃—O—φ—CH₂— | CH₃O(α+β) | Hg(OAc)₂ | CH₃OH | 25° |
| φ—S—CH₂—CONH | CH₃CH₂ | t-butyl | CH₃O(α+β) | Hg(OAc)₂ | CH₃OH | 25° |

TABLE II-continued

| R₁ | R₂ | R₃ | R₅ | Catalyst | Solvent | Temp. |
|---|---|---|---|---|---|---|
| cyclohexyl-CONH | CH₃ | CH₃O-C₆H₄-CH₂ | CH₃O(α+β) | Hg(OAc)₂ | CH₃OH | 25° |
| furan-CH₂-CONH | CH₃CH₂ | t-butyl | CH₃O(α+β) | Hg(OAc)₂ | CH₃OH | 25° |
| phthalimido-N | CH₃ | t-butyl | CH₃O(α+β) | Hg(OAc)₂ | CH₃OH | 25° |
| C₆H₅-CH₂CONH | CH₃ | t-butyl | N₃(α+β) | Hg(OAc)₂ | NaN₃ in DMF | 25° |
| thiophene-CH₂CONH | CH₃ | t-butyl | N₃(α+β) | Hg(OAc)₂ | NaN₃ in TMU* | 25° |
| C₆H₅-CH₂-CONH | CH₃ | t-butyl | CH₃CH₂O(α+β) | Hg(OAc)₂ | CH₃OH | 25° |
| thiophene-CH₂-CONH | CH₃ | CH₃O-C₆H₄-CH₂ | CH₃CH₂O(α+β) | Hg(OAc)₂ | CH₃CH₂OH | 60° |
| C₆H₅-CH₂-CONH | CH₃ | t-butyl | CH₃CO₂(α) | Hg(OAc)₂ | THF | 25° |
| thiophene-CH₂-CONH | CH₃ | t-butyl | CH₃CO₂(α+β) | Hg(OAc)₂ | DME | 40° |
| C₆H₅-CH(NH₂)-CONH | CH₃ | CH₃ | CH₃CO₂(α) | Hg(OAc)₂ | Dioxane-HOAc | 25° |
| C₆H₅-CH₂-CONH | CH₃ | C₆H₅ | CH₃O(α+β) | Hg(OAc)₂ | CH₃OH | 25° |
| C₆H₅-CH₂-CONH | CH₃ | t-butyl | CH₃O(α) | Hg(OMe)₂ | CH₃OH | 25° |
| C₆H₅-CH₂-CONH | CH₃ | t-butyl | CH₃CO₂(α) | Tl(OAc)₃ | DME-HOAc | 25° |
| thiophene-CH₂-CONH | CH₃ | CH₃O-C₆H₄-CH₂ | CH₃CO₂(α) | Tl(OAc)₃ | Dioxane-HOAc | 25° |
| C₆H₅-CH₂-CONH | CH₃ | t-butyl | CH₃O(α) | AgBF₄ | CH₃OH | 25° |
| C₆H₅-CH₂-CONH | CH₃ | t-butyl | (CH₃)₂N-(α+β) | Hg(OAc)₂ | (CH₃)₂NH, DMF | 25° |
| thiophene-CH₂-CONH | CH₃CH₂ | t-butyl | CH₃O(α) | AgBF₄ | CH₃OH | 25° |
| 2,6-dimethoxy-C₆H₃-CONH | CH₃ | CH₃O-C₆H₄-CH₂ | CH₃CH₂O(α) | AgBF₄ | CH₃CH₂OH | Reflux |
| C₆H₅-O-CH₂-CONH | CH₃ | t-butyl | CH₃O(α) | AgClO₄ | CH₃OH | 25° |
| C₆H₅-CH(NH)-C(CH₃)=CH-CO-OCH₃ | CH₃ | CH₃ | CH₃O(α) | AgNO₃ | CH₃OH | 25° |
| C₆H₅-CH(NH₂)-CONH | CH₃ | t-butyl | CH₃CO₂(α+β) | AgOAc | HOAc | 25° |
| C₆H₅-CH₂-CONH | CH₃ | t-butyl | CH₃CO₂(α+β) | Pb(OAc)₄ | DME-HOAc | 25° |

TABLE II-continued

| R₁ | R₂ | R₃ | R₅ | Catalyst | Solvent | Temp. |
|---|---|---|---|---|---|---|
| Ph-CH=N- | CH₃ | t-butyl | CH₃O(α) | Hg(OAc)₂ | CH₃OH | 25° |
| Ph-CH=N- | CH₃ | t-butyl | CH₃CH₂O(α) | Hg(OAc)₂ | CH₃CH₂OH | Reflux |
| CH₃O-Ph-CH=N- | CH₃CH₂ | t-butyl | CH₃O(α) | Hg(OAc)₂ | CH₃OH | 25° |
| O₂N-Ph-CH=N- | Ph- | CH₃O-Ph-CH₂- | CH₃CH₂O(α) | Hg(OAc)₂ | CH₃CH₂OH | Reflux |
| Ph-CH=N | CH₃ | t-butyl | AcO(α) | Hg(OAc)₂ | DME | 25° |
| Ph-CH=N | CH₃ | t-butyl | N₃(α) | Hg(OAc)₂ | NaN₃ in DMF | 25° |
| O₂N-Ph-CH=N | CH₃ | CH₃O-Ph-CH₂ | N₃(α) | AgBF₄ | NaN₃ in DMF | 25° |
| O₂N-Ph-CH=N- | CH₃ | t-butyl | AcO(α) | Hg(OAc)₂ | Dioxane | 25° |
| Ph-CH=N- | CH₃ | t-butyl | CH₃O(α) | AgBF₄ | CH₃OH | 25° |
| Ph-CH=N- | CH₃ | t-butyl | AcO(α) | Tl(OAc)₃ | DME | 25° |
| Ph-CH=N- | CH₃ | t-butyl | (CH₃)₂N-(α+β) | Hg(OAc)₂ | (CH₃)₂NH, DMF | 25° |

*TMU = Tetramethylurea

What is claimed is:

1. A process for preparing a compound of the formula:

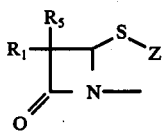

wherein Z is

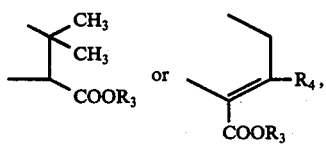

$R_1$ is selected from the group consisting of phthalimido, benzalimino, substituted benzalimino,

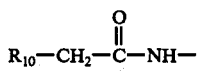

wherein $R_{10}$ is selected from the group consisting of phenyl, substituted phenyl, 1,4-cyclohexadienyl, phenoxy, substituted phenoxy, thienyl, furyl, phenylthio and substituted phenylthio,

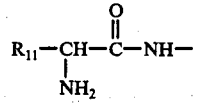

wherein $R_{11}$ is selected from the group consisting of phenyl, substituted phenyl, and 1,4-cyclohexadienyl, and

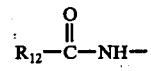

wherein $R_{12}$ is selected from the group consisting of lower alkyl, phenyl and substituted phenyl, and wherein said benzalimino, phenyl, phenoxy, or phenylthio substituent is one or two members selected from the group consisting of lower alkyl, lower alkoxy, nitro, chloro, fluoro and trifluoromethyl; $R_3$ is selected from the group consisting of hydrogen, t-butyl, trichloroethyl, trimethylsilyl, p-methoxybenzyl, and a cation selected from the group consisting of Na⁺, Ca⁺⁺, Li⁺, K⁺, NH₄⁺, and (C₂H₅)NH⁺; $R_4$ is selected from the group consisting of methyl, acetoxymethyl, and carbamoyloxymethyl; and $R_5$ is selected from the group consisting of lower alkoxy, phenoxy, benzoyloxy, lower alkanoyloxy, amino, lower alkylamino, lower dialkylamino, and azido; which comprises reacting a compound of the formula

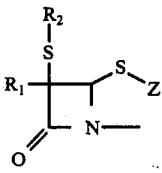

wherein $R_2$ is selected from the group consisting of lower alkyl, phenyl, phenyl-lower alkyl and substituted phenyl or phenyl-lower alkyl wherein said phenyl substituent is one or two members selected from the group consisting of lower alkyl, lower alkoxy, nitro, chloro, fluoro and trifluoromethyl; with a compound selected from the group consisting of a lower alkyl alcohol, phenol, lower alkanoic acid or its heavy metal salt, sodium azide, potassium azide, ammonia, lower alkylamine, and lower dialkylamine in the presence of an effective catalytic amount of a catalyst selected from the group consisting of mercuric acetate, mercuric chloride, dimethoxy mercury, thallium acetate, silver tetrafluoroborate, silver acetate, lead acetate, silver nitrate, and silver perchlorate.

2. A process for the preparation of compounds of the formula:

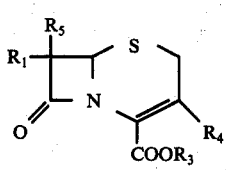

wherein $R_1$ is selected from the group consisting of phthalimido, benzalimino, substituted benzalimino,

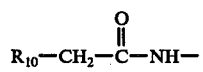

wherein $R_{10}$ is selected from the group consisting of phenyl, substituted phenyl, 1,4-cyclohexadienyl, phenoxy, substituted phenoxy, thienyl, furyl, phenylthio and substituted phenylthio,

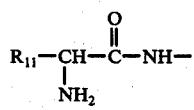

wherein $R_{11}$ is selected from the group consisting of phenyl, substituted phenyl, and 1,4-cyclohexadienyl, and

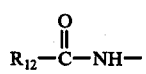

wherein $R_{12}$ is selected from the group consisting of lower alkyl, phenyl and substituted phenyl, and wherein said benzalimino, phenyl, phenoxy, or phenylthio substituent is one or two members selected from the group consisting of lower alkyl, lower alkoxy, nitro, chloro, fluoro and trifluoromethyl; $R_3$ is selected from the group consisting of hydrogen, t-butyl, trichloroethyl, trimethylsilyl, p-methoxybenzyl, and a cation selected from the group consisting of Na+, Ca++, Li+, K+, NH$_4$+, and (C$_2$H$_5$)$_3$NH+; $R_4$ is selected from the group consisting of methyl, acetoxymethyl, and carbamoyloxymethyl; and $R_5$ is selected from the group consisting of lower alkoxy, phenoxy, benzoyloxy, lower alkanoyloxy, amino, lower alkylamino, lower dialkylamino, and azido; which comprises reacting a compound of the formula

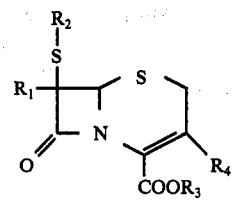

wherein $R_2$ is selected from the group consisting of lower alkyl, phenyl, phenyl-lower alkyl and substituted phenyl or phenyl-lower alkyl wherein said phenyl substituent is one or two members selected from the group consisting of lower alkyl, lower alkoxy, nitro, chloro, fluoro, and trifluoromethyl; with a compound selected from the group consisting of a lower alkyl alcohol, phenol, lower alkanoic acid or its heavy metal salt, sodium azide, potassium azide, ammonia, lower alkylamine, and lower dialkylamine at a temperature of from about −10° C to about 110° C in the presence of an effective catalytic amount of a catalyst selected from the group consisting of mercuric acetate, mercuric chloride, dimethoxy mercury, thallium acetate, silver tetrafluoroborate, silver acetate, lead acetate, silver nitrate, and silver perchlorate.

3. A process for the preparation of compounds of the formula:

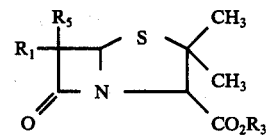

wherein $R_1$ is selected from the group consisting of phthalimido, benzalimino, substituted benzalimino,

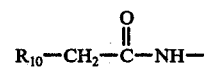

wherein $R_{10}$ is selected from the group consisting of phenyl, substituted phenyl, 1,4-cyclohexadienyl, phenoxy, substituted phenoxy, thienyl, furyl, phenylthio and substituted phenylthio,

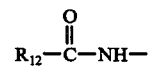

wherein $R_{11}$ is selected from the group consisting of phenyl, substituted phenyl, and 1,4-cyclohexadienyl, and

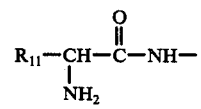

wherein $R_{12}$ is selected from the group consisting of lower alkyl, phenyl and substituted phenyl, and wherein said benzalimino, phenyl, phenoxy, or phenylthio substituent is one or two members selected from the group consisting of lower alkyl, lower alkoxy, nitro, chloro, fluoro and trifluoromethyl; $R_3$ is selected from the group consisting of hydrogen, t-butyl, trichloroethyl, trimethylsilyl, p-methoxybenzyl, and a cation selected from the group consisting of Na+, Ca++, Li+, K+, NH4+, and (C2H5)3NH+; R5 is selected from the group consisting of lower alkoxy, phenoxy, benzoyloxy, lower alkanoyloxy, amino, lower alkylamino, lower dialkylamino, and azido; which comprises reacting a compound of the formula:

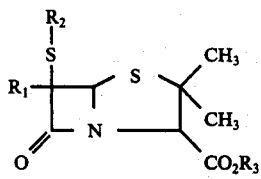

wherein R2 is selected from the group consisting of lower alkyl, phenyl, phenyl-lower alkyl and substituted phenyl or phenyl-lower alkyl wherein said phenyl substituent is one or two members selected from the group consisting of lower alkyl, lower alkoxy, nitro, chloro, fluoro, and trifluoromethyl; with a compound selected from the group consisting of a lower alkyl alcohol, phenol, lower alkanoic acid or its heavy metal salt, sodium azide, potassium azide, ammonia, lower alkylamine, and lower dialkylamine at a temperature of from about −10° C to about 110° C in the presence of an effective catalytic amount of a catalyst selected from the group consisting of mercuric acetate, mercuric chloride, dimethoxy mercury, thallium acetate, silver tetrafluoroborate, silver acetate, lead acetate, silver nitrate, and silver perchlorate.

4. The process of claim 2 wherein $R_1$ is selected from the group consisting of benzalimino, p-nitrobenzalimino, p-methoxybenzalimino, thienylacetamido, α-aminophenylacetamido, α-amino-1,4-cyclohexadienylacetamido, phenylacetamido, and phenoxyacetamido; and $R_5$ is selected from the group consisting of lower alkoxy, lower alkanoyloxy, and azido.

5. The process of claim 4 wherein $R_2$ is selected from the group consisting of lower alkyl, phenyl and substituted phenyl wherein said substituent is one or two members selected from the group consisting of lower alkyl, lower alkoxy, chloro, fluoro, nitro, and trifluoromethyl; and $R_5$ is selected from the group consisting of methoxy, ethoxy, acetoxy, and azido.

6. The process of claim 5 wherein said catalyst is selected from the group consisting of mercuric acetate, dimethoxy mercury and silver tetrafluoroborate.

7. The process of claim 6 wherein $R_2$ is selected from the group consisting of methyl, ethyl, phenyl, 2,4-dinitrophenyl and 4-nitrophenyl.

8. The process of claim 7 wherein $R_1$ is phenylacetamido; $R_5$ is methoxy; $R_3$ is t-butyl; $R_4$ is methyl; $R_2$ is methyl; the reactant is methanol; and the catalyst is mercuric acetate or mercuric chloride.

9. The process of claim 7 wherein $R_1$ is phenylacetamido; $R_5$ is acetoxy; $R_3$ is t-butyl; $R_4$ is methyl; $R_2$ is methyl; and the reactant which also serves as the catalyst is mercuric acetate.

10. The process of claim 7 wherein $R_1$ is benzalimino; $R_5$ is methoxy; $R_4$ is methyl; $R_3$ is t-butyl; $R_2$ is methyl; the reactant is methanol; and the catalyst is mercuric acetate.

11. The process of claim 7 wherein $R_1$ is benzalimino; $R_5$ is ethoxy; $R_3$ is t-butyl; $R_4$ is methyl; $R_2$ is methyl; the reactant is ethanol; and the catalyst is mercuric acetate.

12. The process of claim 7 wherein $R_1$ is phenylacetamido; $R_5$ is methoxy; $R_3$ is t-butyl; $R_4$ is acetoxymethyl; $R_2$ is methyl; the reactant is methanol; and the catalyst is mercuric acetate.

13. The process of claim 3 wherein $R_1$ is selected from the group consisting of benzalimino, p-nitrobenzalimino, p-methoxybenzalimino, thienylacetamido, α-aminophenylacetamido, α-amino-1,4-cyclohexadienylacetamido, phenylacetamido, and phenoxyacetamido; and $R_5$ is selected from the group consisting of lower alkoxy, lower alkanoyloxy, and azido.

14. The process of claim 13 wherein $R_2$ is selected from the group consisting of lower alkyl, phenyl and substituted phenyl wherein said substituent is one or two members selected from the group consisting of lower alkyl, lower alkoxy, chloro, fluoro, nitro, and trifluoromethyl; and $R_5$ is selected from the group consisting of methoxy, ethoxy, acetoxy, and azido.

15. The process of claim 14 wherein said catalyst is selected from the group consisting of mercuric acetate, dimethoxy mercury and silver tetrafluoroborate.

16. The process of claim 15 wherein $R_2$ is selected from the group consisting of methyl, ethyl, phenyl, 2,4-dinitrophenyl and 4-nitrophenyl.

17. The process of claim 16 wherein $R_1$ is phenylacetamido; $R_5$ is methoxy; $R_3$ is p-methoxybenzyl; $R_2$ is methyl; the reactant is methanol; and the catalyst is mercuric acetate or mercuric chloride.

18. The process of claim 16 wherein $R_1$ is phenylacetamido; $R_5$ is acetoxy; $R_3$ is p-methoxybenzyl; $R_2$ is methyl; and the reactant which also serves as the catalyst is mercuric acetate.

19. The process of claim 16 wherein $R_1$ is benzalimino; $R_5$ is methoxy; $R_3$ is hydrogen; $R_2$ is methyl; the reactant is methanol; and the catalyst is mercuric acetate.

20. The process of claim 16 wherein $R_1$ is benzalimino; $R_5$ is ethoxy; $R_3$ is p-methoxybenzyl; $R_2$ is methyl; the reactant is ethanol; and the catalyst is mercuric acetate.

21. The process of claim 16 wherein $R_1$ is phenylacetamido; $R_5$ is methoxy; $R_3$ is p-methoxybenzyl; $R_2$ is methyl; the reactant is methanol; and the catalyst is silver tetrafluoroborate.

22. The process of claim 1 wherein $R_1$ is selected from the group consisting of benzalimino, p-nitrobenzalimino, p-methoxybenzalimino, thienylacetamido, α-aminophenylacetamido, α-amino-1,4-cyclohexadienylacetamido, phenylacetamido, and phenoxyacetamido; $R_5$ is lower alkoxy; $R_2$ is lower alkyl; and the reactant is a lower alkyl alcohol.

23. The process of claim 22 wherein the catalyst is a silver ion.

UNITED STATES PATENT AND TRADEMARK OFFICE
CERTIFICATE OF CORRECTION

PATENT NO. : 4,062,842
DATED : December 13, 1977
INVENTOR(S) : Joseph E. Dolfini et al.

It is certified that error appears in the above-identified patent and that said Letters Patent are hereby corrected as shown below:

Col. 7, line 50, "1960" should read --1690--.

Signed and Sealed this

Twentieth Day of March 1979

[SEAL]

Attest:

RUTH C. MASON
Attesting Officer

DONALD W. BANNER
Commissioner of Patents and Trademarks